US011712352B2

United States Patent
Joye et al.

(10) Patent No.: US 11,712,352 B2
(45) Date of Patent: *Aug. 1, 2023

(54) SYSTEMS AND METHODS FOR DEPLOYING A LUMINAL PROSTHESIS OVER A CARINA

(71) Applicant: Karyna of Arizona, LLC, Phoenix, AZ (US)

(72) Inventors: Jim Joye, Saratoga, CA (US); Michael Fourkas, Sunnyvale, CA (US); Shuji Uemura, San Francisco, CA (US); James Silver, Palo Alto, CA (US); Alison Acly, Santa Clara, CA (US)

(73) Assignee: Karyna of Arizona, LLC, Phoenix, AZ (US)

(*) Notice: Subject to any disclaimer, the term of this patent is extended or adjusted under 35 U.S.C. 154(b) by 344 days.

This patent is subject to a terminal disclaimer.

(21) Appl. No.: 16/901,301

(22) Filed: Jun. 15, 2020

(65) Prior Publication Data

US 2020/0306065 A1    Oct. 1, 2020

Related U.S. Application Data

(63) Continuation of application No. 15/472,107, filed on Mar. 28, 2017, now Pat. No. 10,716,690, which is a
(Continued)

(51) Int. Cl.
*A61F 2/856* (2013.01)
*A61F 2/954* (2013.01)
(Continued)

(52) U.S. Cl.
CPC ............... *A61F 2/856* (2013.01); *A61F 2/07* (2013.01); *A61F 2/844* (2013.01); *A61F 2/954* (2013.01);
(Continued)

(58) Field of Classification Search
CPC .... A61F 2/954; A61F 2/856; A61F 2002/828; A61F 2220/0075; A61F 2220/0091;
(Continued)

(56) References Cited

U.S. PATENT DOCUMENTS

| 4,995,868 A | 2/1991 | Brazier |
| 5,376,094 A | 12/1994 | Kline |

(Continued)

FOREIGN PATENT DOCUMENTS

| EP | 0698380 B1 | 2/2002 |
| JP | H0866480 A | 3/1996 |

(Continued)

OTHER PUBLICATIONS

International search report and written opinion dated Feb. 23, 2015 for PCT Application No. US2014/056656.
(Continued)

*Primary Examiner* — Julian W Woo
(74) *Attorney, Agent, or Firm* — Wilson Sonsini Goodrich & Rosati

(57) ABSTRACT

A system for deploying a prosthesis over a Carina between an ipsilateral lumen and a contralateral lumen includes a guidewire, a guidewire capture catheter, a self-expanding tubular prosthesis, and a delivery catheter. The guidewire is first placed in the ipsilateral lumen. The guidewire capture catheter is then advanced from the contralateral lumen to a position at or above the ipsilateral lumen. The guidewire is typically advanced through an occlusion, which may be a total occlusion, and captured by a capture element on the guidewire capture catheter. The guidewire capture catheter pulls the guidewire out through the contralateral side, and the guidewire is used to advance a delivery catheter from the ipsilateral side. The delivery catheter delivers a first segment
(Continued)

of the tubular prosthesis in the ipsilateral lumen and a second segment of the prosthesis in the contralateral lumen.

8 Claims, 13 Drawing Sheets

Related U.S. Application Data continuation of application No. 14/491,464, filed on Sep. 19, 2014, now Pat. No. 9,636,242.

(60) Provisional application No. 61/880,033, filed on Sep. 19, 2013, provisional application No. 61/887,185, filed on Oct. 4, 2013.

(51) Int. Cl.
*A61F 2/07* (2013.01)
*A61F 2/97* (2013.01)
*A61F 2/844* (2013.01)
*A61F 2/966* (2013.01)
*A61F 2/82* (2013.01)
*A61M 25/00* (2006.01)
*A61M 25/01* (2006.01)
*A61M 25/09* (2006.01)
*A61F 2/06* (2013.01)

(52) U.S. Cl.
CPC ............... *A61F 2/966* (2013.01); *A61F 2/97* (2013.01); *A61F 2002/065* (2013.01); *A61F 2002/828* (2013.01); *A61F 2210/0014* (2013.01); *A61F 2220/0075* (2013.01); *A61F 2220/0091* (2013.01); *A61M 25/0082* (2013.01); *A61M 25/09* (2013.01); *A61M 2025/0175* (2013.01); *A61M 2025/09125* (2013.01); *A61M 2210/127* (2013.01)

(58) Field of Classification Search
CPC ..... A61F 2/07; A61F 2/97; A61M 2025/0175; A61M 2210/127; A61M 25/008
See application file for complete search history.

(56) References Cited

U.S. PATENT DOCUMENTS

| 5,868,754 | A | 2/1999 | Levine et al. |
|---|---|---|---|
| 5,972,019 | A | 10/1999 | Engelson et al. |
| 6,143,002 | A | 11/2000 | Vietmeier |
| 6,200,339 | B1 * | 3/2001 | Leschinsky ............... A61F 2/07 623/1.35 |
| 6,440,161 | B1 | 8/2002 | Madrid et al. |
| 6,632,197 | B2 | 10/2003 | Lyon |
| 6,689,157 | B2 | 2/2004 | Madrid et al. |
| 6,878,151 | B2 | 4/2005 | Carrison et al. |
| 7,674,284 | B2 * | 3/2010 | Melsheimer ............... A61F 2/07 623/1.13 |
| 8,206,427 | B1 | 6/2012 | Ryan et al. |
| 8,475,513 | B2 | 7/2013 | Sithian |
| 9,259,340 | B2 | 2/2016 | Heuser et al. |
| 9,636,242 | B2 | 5/2017 | Joye et al. |
| 10,039,657 | B2 | 8/2018 | Fleming |
| 10,716,690 | B2 | 7/2020 | Joye et al. |
| 2002/0032457 | A1 | 3/2002 | Sirhan et al. |
| 2002/0193824 | A1 | 12/2002 | Boylan et al. |
| 2003/0065354 | A1 | 4/2003 | Boyle et al. |
| 2003/0236566 | A1 | 12/2003 | Heuser |
| 2004/0102719 | A1 | 5/2004 | Keith et al. |
| 2004/0148005 | A1 | 7/2004 | Heuser |
| 2005/0033416 | A1 | 2/2005 | Seguin et al. |
| 2005/0177222 | A1 | 8/2005 | Mead |
| 2005/0234542 | A1 | 10/2005 | Melsheimer et al. |
| 2006/0047222 | A1 | 3/2006 | Heuser |
| 2006/0161244 | A1 | 7/2006 | Seguin |
| 2006/0178733 | A1 | 8/2006 | Pinchuk et al. |
| 2007/0173878 | A1 | 7/2007 | Heuser |
| 2008/0065019 | A1 | 3/2008 | Heuser et al. |
| 2008/0161901 | A1 | 7/2008 | Heuser et al. |
| 2008/0288045 | A1 | 11/2008 | Saeed |

FOREIGN PATENT DOCUMENTS

| JP | 2002538852 A | 11/2002 |
|---|---|---|
| JP | 2005510293 A | 4/2005 |
| JP | 2006525063 A | 11/2006 |
| JP | 2007514498 A | 6/2007 |
| JP | 2008518710 A | 6/2008 |
| JP | 2012501734 A | 1/2012 |
| JP | 3173368 U | 2/2012 |
| WO | WO-0020064 A1 | 4/2000 |
| WO | WO-0033769 A1 | 6/2000 |
| WO | WO-03045283 A1 | 6/2003 |
| WO | WO-2004096092 A1 | 11/2004 |
| WO | WO-2005058202 A1 | 6/2005 |
| WO | WO-2006072835 A3 | 7/2006 |
| WO | WO-2010027677 A1 | 3/2010 |
| WO | WO-2015042467 A1 | 3/2015 |

OTHER PUBLICATIONS

Notice of Allowance dated Mar. 13, 2020 for U.S. Appl. No. 15/472,107.
Notice of Allowance dated Dec. 29, 2016 for U.S. Appl. No. 14/491,464.
Office action dated Feb. 6, 2019 for U.S. Appl. No. 15/472,107.
Office Action dated May 23, 2016 for U.S. Appl. No. 14/491,464.
Office action dated Sep. 5, 2019 for U.S. Appl. No. 15/472,107.

* cited by examiner

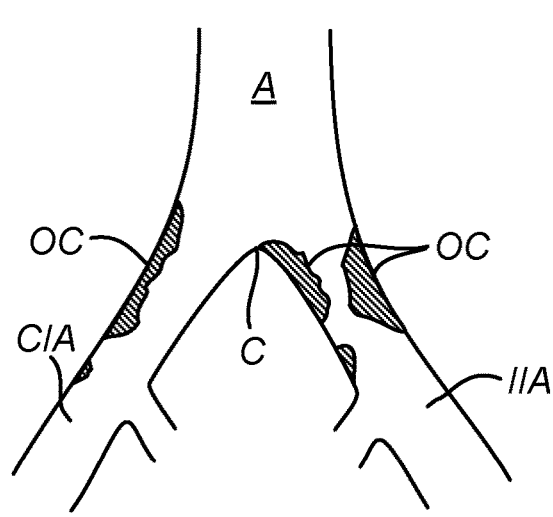
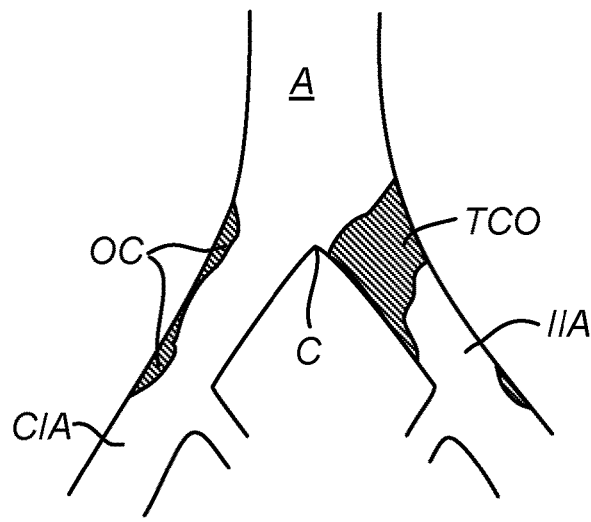
FIG. 1A  FIG. 1B
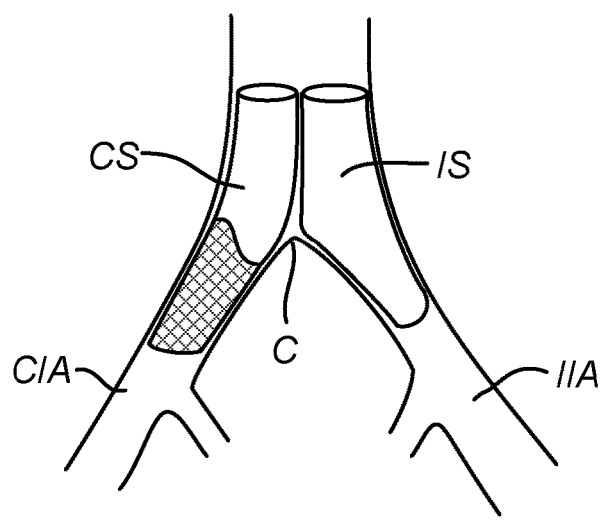
FIG. 2
*(PRIOR ART)*

SYSTEMS AND METHODS FOR DEPLOYING A LUMINAL PROSTHESIS OVER A CARINA

CROSS-REFERENCE

This application is a continuation of U.S. patent application Ser. No. 15/472,107, filed Mar. 28, 2017, which is a continuation of U.S. patent application Ser. No. 14/491,464, filed Sep. 19, 2014, now U.S. Pat. No. 9,636,242, which claims the benefit of provisional application 61/880,033, filed on Sep. 19, 2013, and of provisional application 61/887,185, filed on Oct. 4, 2013, the full disclosures of which are incorporated herein by reference.

BACKGROUND OF THE INVENTION

1. Field of the Invention

The present invention relates generally to medical systems and methods. More particularly, the present invention relates to systems and methods for stenting aortic and other bifurcations while preserving contralateral arterial access.

The use of endoluminal prostheses for treating vascular and other diseases has become wide-spread over the past several decades. Endoluminal prostheses, commonly known as stents, are used to maintain the patency of blood vessels and other body lumens. Stents are typically formed as tubular metal scaffolds which can be expanded in situ from a relatively small diameter to a larger diameter sufficient to maintain the desired level of patency. The stents or other vessel scaffolds can be covered with fabrics or membranes, in which case they are commonly referred to grafts.

The use of both stents and grafts has become wide-spread and has revolutionized many medical treatments. Despite the wide success, the treatment of certain anatomies still presents challenges. For example, the treatment of atherosclerotic lesions in bifurcated blood vessels, where a main vessel divides into two branches, can be difficult. For example, occlusive disease frequently occurs at the bifurcation of the aorta into the iliac arteries. While such bifurcation disease may be successfully treated by using a pair of vascular grafts where one graft is placed in each iliac artery and the grafts are disposed side-by-side in the aorta (commonly referred to as "kissing stents"), such treatment makes subsequent contralateral access to treat future disease more difficult.

Referring to FIGS. 1A and 1B, the nature of occlusive disease which occurs at the bifurcation of an aorta A into an ipsilateral iliac artery IIA and a contralateral ipsilateral artery CIA will be described. The occlusive disease may be only partial, as illustrated in FIG. 1A, where the lumen of neither the ipsilateral nor the contralateral iliac arteries is fully occluded. In other cases, as illustrated in FIG. 1B, at least one of the ipsilateral and contralateral iliac lumens will be completely blocked, referred to as a chronic total occlusion CTO. Treatments for these two different conditions will vary, as described in detail below in connection with the present invention. Presently, however, for both conditions the most common treatments is the placement of an ipsilateral stent or graft IS in the ipsilateral iliac artery IIA and a contralateral stent or graft CS in the contralateral iliac artery CIA, as shown in FIG. 2 (the so-called kissing stents referred to earlier). While the resulting stent or graft structures provide excellent recanalization of the aorta and the branching iliac arteries, the structure also makes it very difficult to achieve subsequent contralateral access from an ipsilateral iliac artery. Without the stent or graft structures in place, it will be appreciated that a guidewire placed in through an ipsilateral iliac artery can be easily passed over the carina C into a contraleteral iliac artery once the occlusive disease has been penetrated or bypassed. The "kissing stents" IS and CS, in contrast, form a boundary between the iliac arteries that makes it very difficult to advance a guidewire from the ipsilateral iliac artery IIA to the contralateral iliac artery CIA. Thus, subsequent treatment of disease at or near the aortic bifurcation can be much more difficult, often requiring open surgery rather than an endoluminal treatment.

For these reasons, it would be desirable to provide improved systems and methods for treating occlusive and other disease at the aortic and other vascular and non-vascular vessel bifurcations. The systems and methods should be able to provide the improved patency achieved by the "kissing stents" of the prior art, while preserving the ability to subsequently access a contralateral lumen from an ipsilateral lumen by advancing a guidewire over the carina with minimum inhibition. The methods and systems should be compatible with both totally and partially occluded lumens, and in the case of aortic disease, it should facilitate passage of a guidewire through a totally occluded ipsilateral iliac artery into a contralateral iliac artery. At least some of these objectives will be met by the inventions described below.

2. Description of the Background Art

Systems and methods for manipulating guidewires and bypassing occlusions in the peripheral vasculature are described in US20140142677; US20140142677; US20070173878; US20030236566; US20030236566; US20040148005; US20030161901; US20060047222; US20080065019.

SUMMARY OF THE INVENTION

A principal objective of the present invention is to provide a stenting or grafting structure at an aortic or other bifurcation which is effective to treat occlusive or other disease on either side of the carina in the adjacent branch lumens without blocking or inhibiting subsequent guidewire access from an ipsilateral lumen to a contralateral lumen over the carina. As illustrated in FIG. 3, a tubular prosthesis structure can, according to the present invention, cover the occlusive disease and maintain luminal patency in the adjacent iliac arteries IIA and CIA on either side of the carina C, while maintaining a region or volume above the carina substantially free from structures which would inhibit passage of a guidewire over the carina. In particular, the tubular prosthesis structures of the present invention will avoid creating a wall or other barrier between the iliac arteries as was characteristic of the "kissing stents" shown in FIG. 2 above.

The following paragraphs define a glossary of terms and phrases which are used in the specification and claims herein. Terms and phrases which are not specifically defined herein will have the meanings normally associated with those terms and phrases to one of ordinary skill in the art of endovascular and endoluminal procedures, particularly including interventional radiologists and interventional cardiologists who perform stenting and grafting procedures in the peripheral vasculature.

The phrases "ipsilateral lumen" and "contralateral lumen" will include all vascular and other lumens which branch from a main or a primary vessel or lumen. Of particular interest to the present invention, the aorta branches into a pair of common iliac arteries which subsequently branch into the internal iliac artery, the femoral artery, the popliteal artery, and the like. When the present application refers to introducing a guidewire or catheter into the iliac or any other lumen, that introduction can take place in the noted lumen or in any lumen which is downstream from the noted lumen. In particular, introduction of a guidewire or catheter into the iliac artery will frequently be made via the femoral artery. The designation of ipsilateral lumen and contralateral lumen is somewhat arbitrary. For example, either of the iliac arteries may be designated as the ipsilateral iliac artery, in which case the other iliac artery becomes the contralateral iliac artery. For convenience, as used hereinafter, the ipsilateral lumen or artery will be that lumen into which a crossing guidewire is initially placed and the contralateral lumen or artery will be the lumen into which the crossing guidewire is guided and exits the vasculature.

The phrase "luminal prosthesis" refers to any stent or graft structure which is placed over a carina to treat occlusive or other diseases present in either or both of the iliac arteries or other branching vessels. The luminal prostheses will have a first segment configured to be placed in an ipsilateral lumen and a second segment configured to be placed in a contralateral lumen. The first and second segments will preferably be coupled to each other in such a way that they may be delivered in a straightened or linearized manner, and subsequently bent or folded over the carina in situ to assume their desired positioning in vasculature or other lumens. In some cases, however, it will be possible to deliver first segments which are not coupled and which are independently anchored at their target locations in the branching lumens.

The luminal prostheses of the present invention will preferably be self-expanding. By "self-expanding" it is meant that the prostheses, which are typically tubular in geometry, may be crimped or constrained to assume a low diameter configuration, typically by placing over a delivery catheter within a constraining, outer sheath. The sheath is retractable, and once the constraint of the sheath is removed, the luminal prosthesis will be able to radially expand due to its own resilience to open within the target vessel and provide the desired support or scaffolding of the vessel. Such self-expanding luminal prostheses are typically formed from a resilient metal, such as nickel-titanium alloy (e.g., Nitinol®) but could also be other shape memory metals or a resilient polymer.

On treating a chronic total occlusion, it will often be necessary to "subintimally" advance the guidewire past the occlusion. Such "subintimal advancement" means that the guidewire passes out of the vascular or other vessel lumen into the region between the vascular wall and the intimal tissue. The virtual space between these layers, which are typical of the arterial vasculature, provides an advancement path which bypasses the occlusion. It is necessary that, once past the occlusion, the guidewire be passed or directed back into the vessel lumen. In some cases, the present invention can use conventional guidewire advancement systems, such as the Pioneer® system available from Volcano. Preferably, however, return of the subintimally advanced guidewire into the iliac or aorta (or other vasculature or non-vasculature) lumen will be accomplished by a guidewire capture catheter which is described and claimed herein.

The guidewire capture catheter will employ an expandable guidewire capture element which is typically a mechanically expanded cage. The mechanically expanded cage can be a braided structure, a malecot structure, or any other structure which may be expanded by axial foreshortening, electrical stimulation, pull-back using a pull-wire or a cord, rotation using a screw or other mechanism, or the like. In other less preferred cases, the cage may be self-expanding where it is initially constrained within a sheath or other overlying element and released to radially expand when desired. In still other cases, the expandable guidewire capture element can be actuated by an inflatable balloon, typically in combination with a wire cage or lattice structure over the balloon to provide a desired expansion force and guidewire capture capability.

In a first aspect of the present invention, a method for deploying a luminal prosthesis over a carina between an ipsilateral lumen and an contralateral lumen comprises placing a guidewire over the carina between the two lumens. A delivery catheter is advanced over the guidewire and carries the luminal prosthesis, typically a tubular prosthesis, over the carina. The prosthesis is deployed from the delivery catheter so that a first segment of the prosthesis is positioned in the ipsilateral lumen and a second segment of the prosthesis is positioned in the contralateral lumen. The ipsilateral lumen is typically an ipsilateral iliac artery, and the contralateral lumen is typically a contralateral iliac artery. In specific embodiments, the guidewire is placed initially through an ipsilateral femoral artery, and then through the ipsilateral iliac artery and over the carina, where it passes through the contralateral iliac artery and exits through the contralateral femoral artery.

In exemplary embodiments, placing the guidewire comprises advancing the guidewire through the ipsilateral lumen, over the carina, and into the contralateral lumen. In cases where the ipsilateral lumen has a total occlusion near the carina, and particularly in the case of an ipsilateral iliac artery, the guidewire will be advanced through the subintima past the total occlusion in the ipsilateral lumen, prior to being advanced over the carina and into the contralateral lumen. In such cases, a guidewire capture catheter is preferably deployed through the contralateral lumen to position a capture element above an opening of the ipsilateral lumen adjacent the carina. As the guidewire exits the subintima, the capture element both deflects the guidewire back into the vessel lumen and captures the guidewire. By capturing the guidewire, the guidewire capture catheter can then be used to draw the guidewire out through the contralateral lumen and usually further out through the access sheath into the contralateral lumen.

Deploying the capture element typically comprises expanding the capture element, and the capture element will typically be collapsed over the guidewire in order to capture the guidewire and prior to retracting the guidewire from the lumen or vasculature. The capture element may comprise a cage structure, a balloon structure, or any of the mechanisms previously described.

The tubular prosthesis is typically self-expanding and is constrained in a low profile or low diameter configuration on the delivery catheter prior to deployment. Deployment typically comprises retracting an overlying sheath which releases the self-expanding prosthesis from constraint so that it may radially expand at a desired target site in the iliac or other vascular or non-vascular lumen. Preferably, deploying the prosthesis will further comprise the aligning markers on the tubular prosthesis and/or the delivery catheter with specific patient anatomy, usually under fluoroscopy, to position the first segment in the ipsilateral lumen and the second segment in the contralateral lumen prior to deploying the prosthesis, typically by retracting the sheath.

Retracting the sheath may comprise retracting a single sheath in one direction to sequentially release the first and second segments of the tubular prosthesis in a generally conventional manner for the release of self-expanding prostheses. Alternatively and preferably, the sheath may comprise first and second portions or lengths which cover the first and second segments of the tubular prostheses, respectively. The first and second lengths of the sheath may then be retracted into the ipsilateral and contralateral lumens, respectively, in order to separately release the first and second segments of the tubular prostheses. The first and second lengths of the sheath may be retracted simultaneously or sequentially, and in both cases the ability to separately deploy the first and second segments of the tubular prosthesis provides advantages, particularly permitting better placement by allowing each segment to be partially deployed prior to full deployment of either segment.

The first and second segments of the tubular prosthesis are preferably deployed to "tent" over the carina but to open from each other above the carina to define and open, arcuate path between the ipsilateral and contralateral lumens to allow subsequent advancement of the guidewire and/or treatment catheter. While a number of specific prosthesis designs can achieve this objective, it is advantageous that the particular prosthesis designs have little or no structure which would impede advancement of the guidewire or catheter over the carina. In exemplary designs of the tubular prostheses of the present invention, the first and second segments may be joined by a hinge region, by a tether, or in other less preferable embodiments may not be joined at all. In still other embodiments, the tubular prosthesis may be a generally continuous tubular structure where the first and second segments are defined by a side or lateral opening in the tubular prosthesis which expands as the tubular prosthesis is folded or bent over the carina. The opening or fenestration in the stent will preferably have a diameter equal to at least the radius of the stent and could have a diameter equal to the diameter of the stent, or be even larger. By placing the opening or fenestration on the outside of the arc which is formed as the prosthesis is bent over the carina, the opening will significantly expand to provide the open volume, free from structure, over the carina which is desired.

In a second aspect of the present invention, a tubular prosthesis for placement over a carina, between an ipsilateral iliac artery and a contralateral iliac artery comprises a first segment configured to be deployed in the ipsilateral iliac artery and a second segment configured to be deployed in the contralateral iliac artery. The first and second segments are self-expanding and further configured to be delivered in a linearized arrangement within a lumen of a delivery catheter and to be released from the delivery catheter to assume a nonlinear configuration over the carina with an opening directed at an aorta which branches into the iliac arteries.

In specific embodiments, the first and second segments of the tubular prosthesis may each comprise self-expanding metal or polymer scaffolds, and each of the scaffolds is typically at least partially covered by a graft material, such as expanded PTFE, polyethylene membranes, and the like. Exemplary tubular prostheses may have any of the specific geometries described above in connection with the methods of the present invention.

In a further aspect of the present invention, delivery catheters for delivering the tubular prostheses as described above will comprise a catheter body having a distal end and a proximal end. The tubular prosthesis is mounted over the catheter body at a location between the distal and proximal ends so that the prostheses may be positioned over the carina while the distal end of the catheter body extends out of a contralateral lumen while a proximal end of the catheter body remains extending out of the ipsilateral lumen. The self-expanding tubular prosthesis is maintained on the stent by a sheath disposed coaxially over the catheter body to radially constrain both segments of the tubular prosthesis so that retraction of the sheath allows each segment to expand within the respective iliac lumen.

The delivery catheter will be configured for delivery over a 0.035 in wire (0.040"ID) with an 8 Fr profile (0.104" OD). The delivery catheter will typically have a length of 120 cm for over the arch approach with an ipsilateral/contralateral sheath access) or a length of 75 cm for single side, ipsilateral access only. The prostheses will be configured to accommodate iliac limb diameters from 6-12 mm, usually in 1 mm increments and to accommodate aortic diameters from 12-24 mm in 2 mm increments with an aortic portion extending 5-10 mm into the aorta and iliac limb lengths from 3-8 cm in 1 cm increments In some cases, the sheath may comprise a single, continuous structure which at least partially covers both the distal and proximal segments of the tubular prosthesis. This way, the entire sheath may be retracted in a single direction to release both segments of the tubular prosthesis sequentially. Alternatively and preferably, however, the sheath may include at least a distal portion which at least partially covers the distal or second (contralateral) segment of the tubular prosthesis and a proximal segment which at least partially covers the proximal (or ipsilateral) segment of the tubular prosthesis. The distal portion may then be used to distally retract the distal or second segment of the tubular prosthesis while the proximal portion may be retracted to release the proximal or second segment of the tubular prosthesis. Use of such a two-part release sheath has the advantages described above with connection to the methods of the present invention. In yet another aspect of the present invention, a guidewire capture catheter comprises a catheter body having a distal end and a proximal end. An expandable guidewire capture element is disposed on the catheter body, typically near the distal end thereof. The guidewire capture element is configured (1) to be expanded from a small-diameter configuration which permits advancement through an ipsilateral iliac arterial lumen to a space above a carina to a large diameter configuration and (2) to deflect and capture a guidewire emerging from a subintimal passage around an occlusion in a contralateral iliac arterial lumen.

The capture catheters of the present invention will be specifically dimensioned and configured to deploy the expandable guidewire capture element within the lower region of the aorta immediately above the carina and the branching into the right and left iliac arteries. In particular, a catheter will typically have a length in the range from 60 cm to 90 cm, preferably being about 75 cm, and a 7 Fr for delivery over a 0.035 in guidewire. The expandable guidewire capture element will have a diameter when collapsed in the range from 1.5 mm to 2.5 mm, preferably being about 2 mm, and a diameter when fully expanded in the range from 14 mm to 28 mm.

The guidewire capture catheter will be specifically configured so that it may be advanced through a sheath into a contralateral femoral lumen and further through the contralateral iliac lumen, to the space above the carina for deployment of the catheter element. The capture element itself may have any of the configurations discussed generally above. In a still further aspect of the present invention, a system for deploying a prosthesis over a carina between an ipsilateral iliac lumen and a contralateral iliac lumen comprises a guidewire, a guidewire capture catheter, a self-expanding tubular prosthesis, and a delivery catheter. The guidewire will be sized and be sufficiently stiff to be placed through an entry sheath into a femoral artery, over a carina at an aortic bifurcation, and out through an exit sheath in a contralateral femoral artery. The guidewire capture catheter will comprise a catheter body, having an expandable guidewire capture element for the distal end thereof. The self-expanding tubular prosthesis will have a first segment configured to be deployed in the ipsilateral iliac lumen, and a second segment configured to be deployed in the contralateral iliac lumen. The delivery catheter will comprise a catheter body, having a proximal end and a distal end and a retractable sheath. The tubular prosthesis is mounted over the catheter body in a radially constrained configuration beneath the retractable sheath, so that retraction of the sheath allows both segments of the tubular prosthesis to expand within the ipsilateral and contralateral iliac lumens, respectively.

The guidewire preferably has a length in the range from 200 cm to 300 cm and a diameter in the range from 0.8 mm to 1 mm. Further specific aspects of the guidewire capture catheter, the self-expanding tubular prosthesis, and the delivery catheter have been described above with respect to other aspects of the methods and systems of the present invention.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 1A and 1B illustrate an aortic bifurcation into iliac branch arteries showing partially occlusive disease (FIG. 1A), and totally occlusive disease (FIG. 1B).

FIG. 2 illustrates a prior art method for treating occlusive disease at an aortic bifurcation using "kissing" stents.

DETAILED DESCRIPTION OF THE INVENTION

Figure 3:
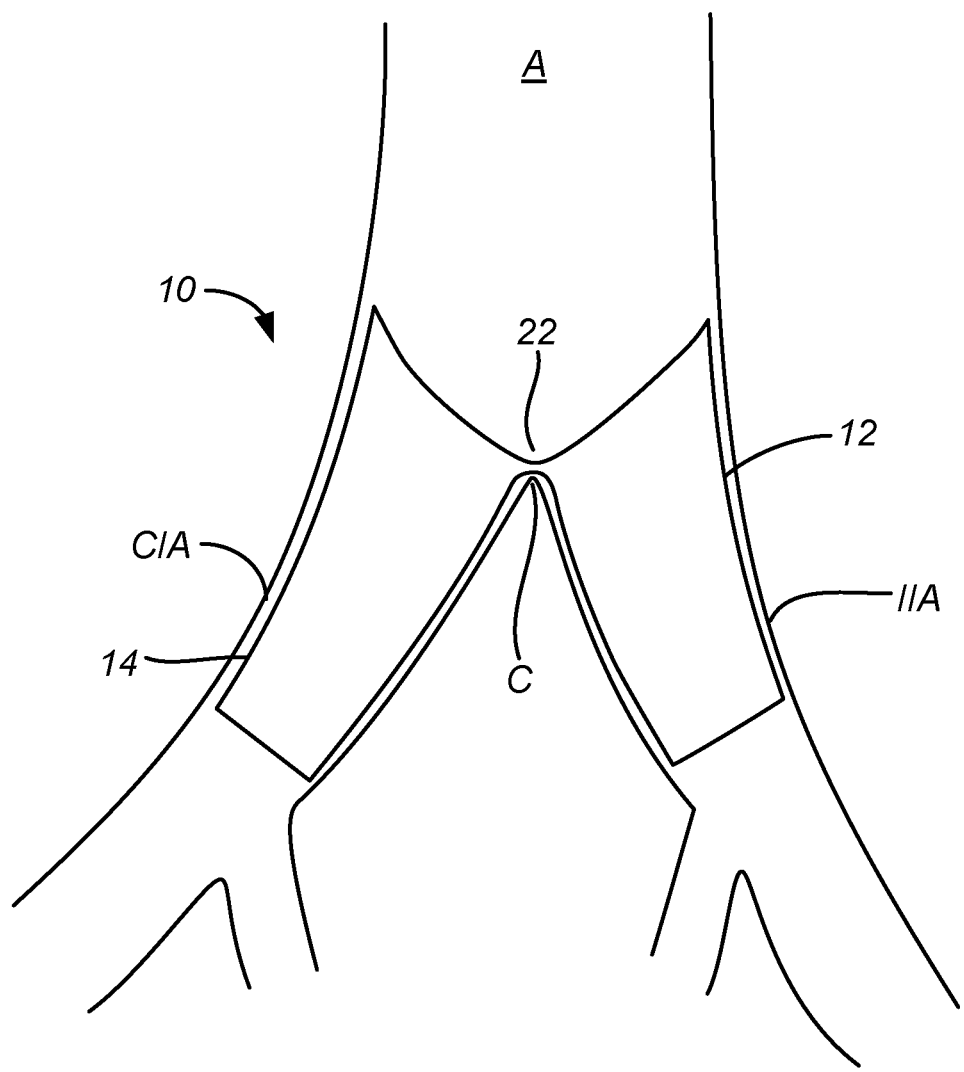
FIG. 3 shows an exemplary placement of a folded or bent tubular prosthesis constructed in accordance with the principals of the present invention providing an open area in the lower aorta which is generally free from structure and allows contralateral access of a guidewire and treatment catheter for contralateral access of a guidewire and a treatment catheter for treatment of future disease which may occur at or near the aortic bifurcation.

Referring again to FIG. 3, an exemplary tubular prosthesis 10 constructed in accordance with the principals of the present invention will comprise a tubular body having a first segment 12 and a second segment 14. For convenience, as shown here and after, the first segment 12 will be placed in the ipsilateral iliac artery IIA, which is the artery through which the crossing guidewire is to be placed. The second segment 14 will be placed in the contralateral iliac artery CIA which is the iliac artery through which the guidewire capture catheter is to be advanced and the crossing guidewire is eventually to be pulled back by the guidewire capture catheter. The tubular prosthesis, when deployed as shown in FIG. 3, will usually have a connecting region 22 which bendable connects the first segment 12 to the second segment 14 at all times, including when the tubular prosthesis 10 is linearized or straightened for delivery (not shown in FIG. 3) and when the prosthesis is bent and fully deployed with the connecting region 22 draped or tented over the carina C as shown in FIG. 3.

Figure 3A:
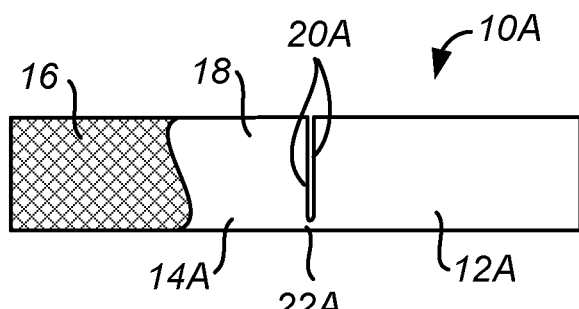
FIGS. 3A and 3B illustrate a first exemplary tubular prosthesis constructed in accordance with the principals of the present invention having a hinged region between first and second segments thereof.
Figure 3B:
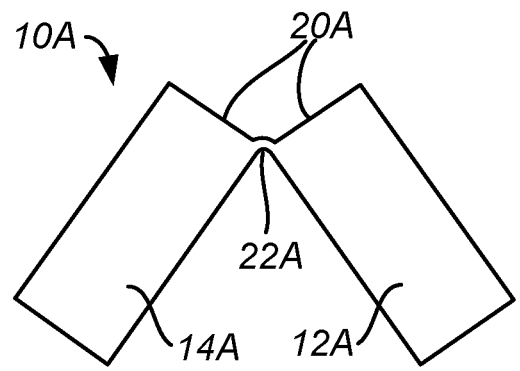

Exemplary embodiments of the tubular prosthesis 10 are shown in FIGS. 3A through 7B. FIGS. 3A and 3B illustrate tubular prosthesis 10A having a first segment 12A connected to a second segment 14A by a hinge region 22A. As shown in FIG. 3B, the hinge region 22A can accommodate bending of the prosthesis and will generally lie over the carina C (FIG. 3) when the stent is deployed. Other features of the tubular prosthesis 10A include a structure comprising and underlying scaffold 16, typically a resilient metal scaffold of the type commonly employed in vascular and non-vascular stents and grafts. Exemplary materials included spring stainless steel and Nitinol®. This scaffold 16 will typically be covered by a graft material which can be any conventional or non-conventional graft material utilized in vascular and non-vascular medical procedures. Exemplary graft materials include expanded PTFE, polyethylenes, and the like. Each of the tubular prostheses 10B-10E described below will usually have a similar structure including an inner scaffold and an outer graft cover.

The inner ends 20A of each of the first and second segments 12A and 14A are shown to be straight and disposed laterally across the prosthesis 10A when the prosthesis is in its linearized configuration. These ends 20A will open into a V-shaped geometry when the stent is folded or bent as shown in FIG. 3B.

Figure 4A:
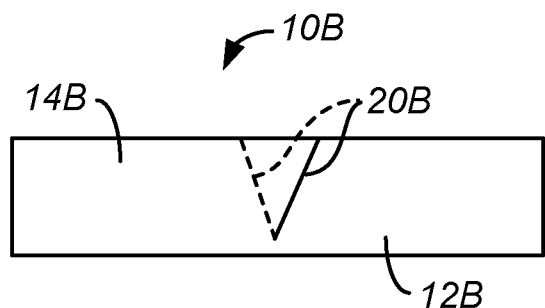
FIGS. 4A and 4B illustrate a similar hinged tubular prosthesis to that shown in FIGS. 3A and 3B but further having curved or arcing ends of each of the first and second segments which overlap when the tubular prosthesis is in a linearized configuration (FIG. 4A) and which open to provide additional wall coverage of the aorta as shown in FIG. 3.
Figure 4B:
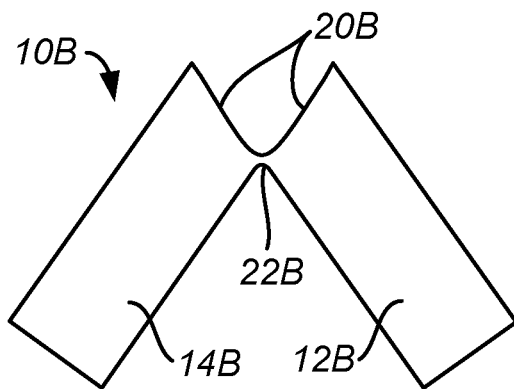

The tubular prosthesis 10B of FIGS. 4A and 4B is very similar to that of the prosthesis of FIGS. 3A and 3B. First segment 12B is joined to second segment 14B by a hinge region 22B. The inner edges 20B of the two segments, however, differ in that they are curved inwardly and overlap when the prosthesis 10B is in its linearized or straightened configuration as shown in FIG. 4A. When the prosthesis 10B is opened by bending or folding, as shown in FIG. 4B, the edges 20B of the first and second prosthesis segments open into a smooth and a continuous arcuate profile similar to that shown in FIG. 3. By curving the ends of the prosthesis segments, the effective coverage on the aortic walls can be increased relative to that provided by the straight end segments 20A of prosthesis 10A. It will be appreciated that other end geometries could be employed to both increase and decrease the coverage of the aortic wall by inclining, curving, or otherwise modifying the shape of the interior ends of the first and second prosthesis segments. Other geometries include castellated ends, zig-zag ends, serpentine ends, and the like.

Figure 5A:
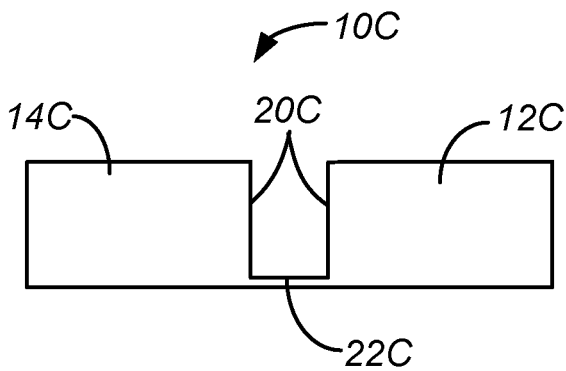
FIGS. 5A and 5B illustrate a further exemplary embodiment of a tubular prosthesis constructed in accordance with the principals of the present invention having first and second segments joined by a short tether.
Figure 5B:
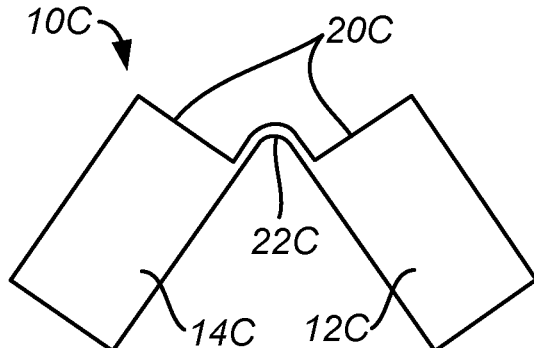
Figure 6A:
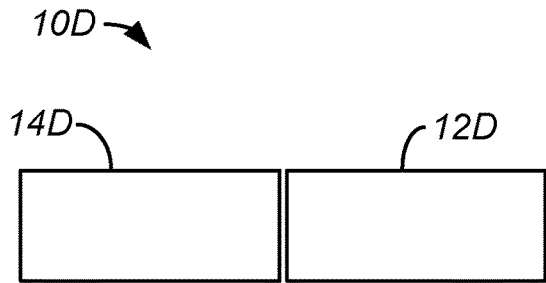
FIGS. 6A and 6B illustrate yet a further embodiment of a tubular prosthesis constructed in accordance with the principals of the present invention where the prosthesis includes first and second segments which are unattached.
Figure 6B:
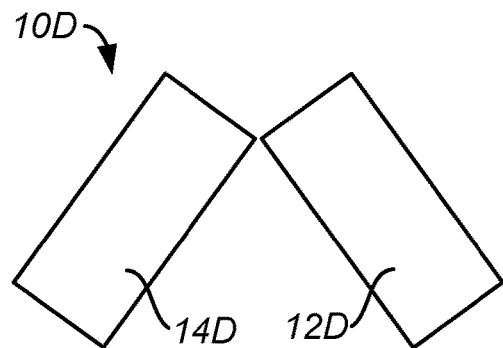

Referring now to FIGS. 5A and 5B, a tubular prosthesis 10C includes a first segment 12C and a second segment 14C joined together by a tether region 22C. The tether 22C can be formed as a part of the underlying scaffold (not shown) or could be later joined to previously manufactured scaffold segments. The tether can bend at its middle, as shown in FIG. 5B, which case the segments 12C and 14C would be generally symmetrically placed in the ipsilateral and contralateral iliac arteries. Using a tether 22C, however, allows the bend point to be shifted which in turn allows a symmetric positioning of the first and second segments in the ipsilateral and contralateral iliacs or other lumens, respectively. The ability to provide such repositioning allows improved treatment of asymmetric diseases in the affricated lumens. The ability to move the edges 20C away from the Carina also allows a user to minimize coverage of the aortic wall should that be desired. Referring now to FIGS. 6A and 6B, in some instances it may be desirable to have no connecting region between a first prosthesis segment 12D and a second prostheses segment 14D. In those instances, the segments may be oriented to accommodate the bifurcation, as shown in FIG. 6B, using the delivery systems of the present invention. Generally, however, it will be preferred to use segments which are joined together by a hinge region, tether, or other coupling structure. In other instances, the first and second segments may be deployed in an unconnected manner and it will be possible to subsequently introduce a connecting region to help pull the relative positions of the segments.

Figure 7A:
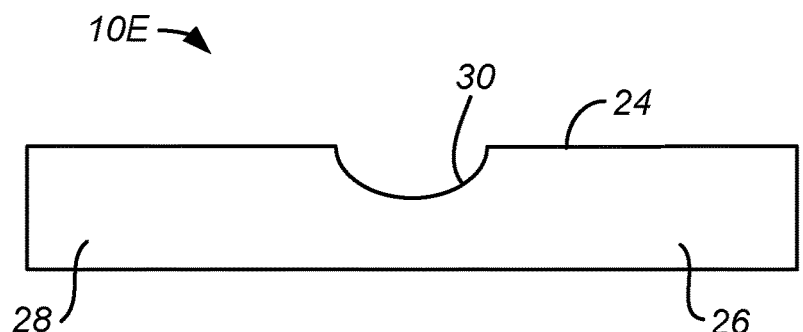
FIGS. 7A and 7B illustrate yet a further embodiment of a tubular prosthesis constructed in accordance with the principals of the present invention where the prosthesis comprises the tubular body having a hole or fenestration on one side thereof.
Figure 7B:
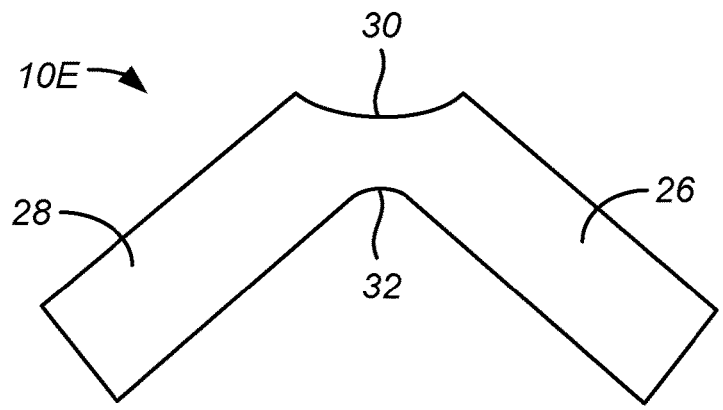

Referring now to FIGS. 7A and 7B, a tubular prosthesis 10E comprises a generally continuous tubular structure 24 having a first segment 26 and a second segment 28. The first and second segments are defined by the presence of an opening or fenestration 30 which will be sized to open to a diameter (as shown in FIG. 7B) which corresponds at least generally to the aortic diameter immediately above the Carina. The scaffold structure of the prosthesis 10E will allow the opening 30 to expand and the closed portion of the tubular body 24 to bend into an arc 32, as shown in FIG. 7B. The tubular prosthesis 10E may be delivered by the delivery systems, as described hereinafter, that will generally not be preferred over the hinged, tethered, or similarly coupled structures described previously.

Figure 8:
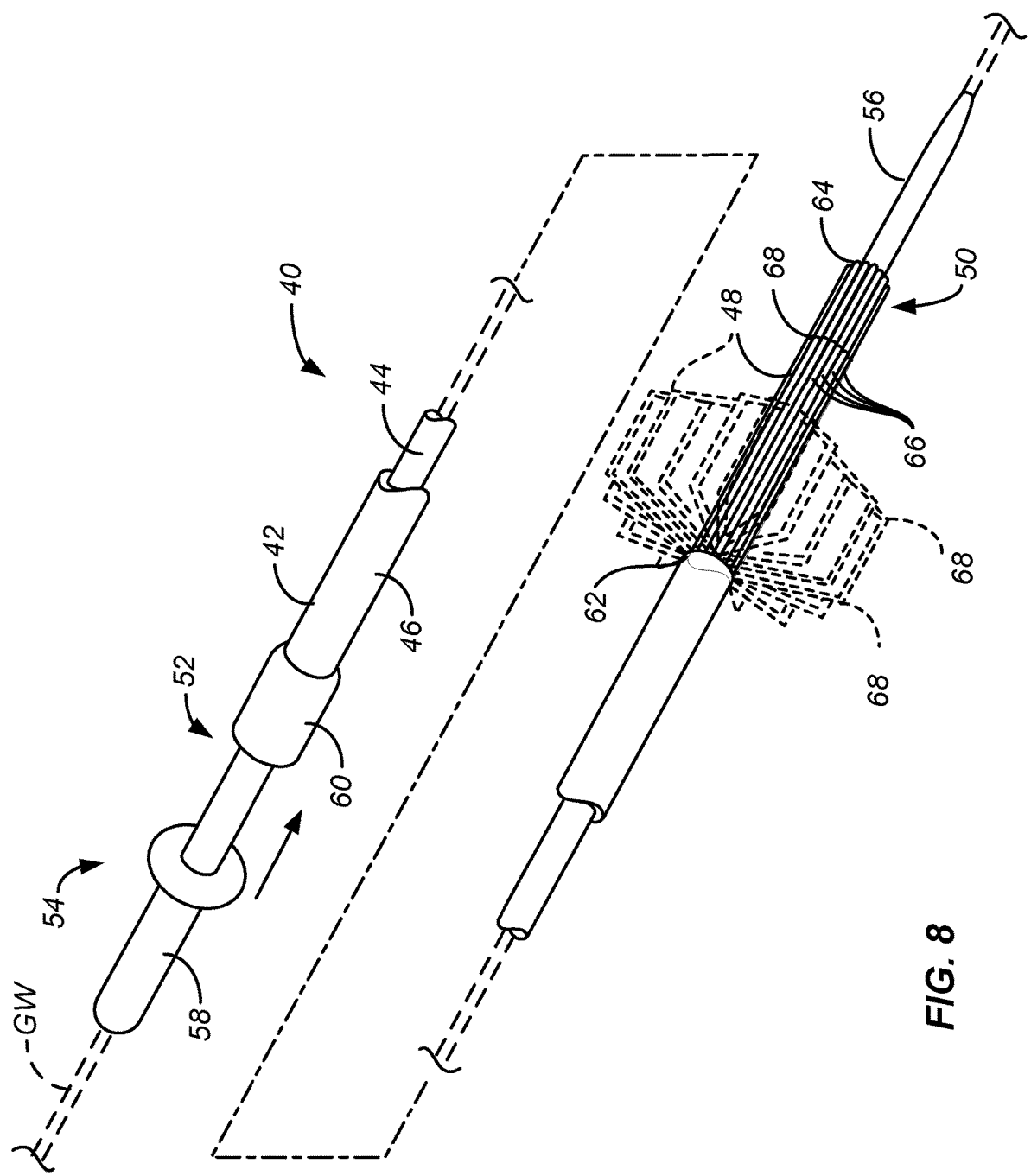
FIG. 8 illustrates an exemplary guidewire capture catheter constructed in accordance with the principals of the present invention.

Referring now to FIG. 8, an exemplary guidewire capture catheter 40 comprises a catheter body 42 having an inner tubular member 44 and an outer tubular member 46. The inner and outer tubular members are arranged coaxially and can axially slide relative to each other in order to deploy an expandable guidewire capture element 48, as described in more detail below. The expandable guidewire capture element is disposed generally at a distal end 50 of the catheter body and a deployment handle assembly 52 is disposed at a proximal end 54 of the catheter body. Usually, an atraumatic tip 56 extends beyond the distal end of the expandable guidewire capture element 48 in order to minimize trauma which could occur if the somewhat rigid capture element were at the tip of the catheter 50. The guidewire capture catheter will be configured to be advanced over a Guidewire followed by reference letters GW, with the guidewire generally passing through an interluminar passage of the inner tubular member 44 and not shown). The guidewire capture element 48 is shown in its low profile or radially collapsed configuration in solid line in FIG. 8. The capture element 48 may be radially expanded into the configuration shown in broken line in FIG. 8 by pushing pusher 48 of the handle assembly relative to a grip 60 at the end of the outer tubular member 46. Pushing the pusher advances the distal end of the inner tubular member 44 which is connected to a proximal end of the expandable guidewire capture element 48. As the distal end 64 of the capture element is attached to the inner tubular member, the capture element is axially foreshortened which forces the radial expansion.

As illustrated in FIG. 8, the expandable guidewire capture element 48 comprises a plurality of axial elements circumferentially distributed over the catheter body 42. Each linear element has weakened regions which preferentially bend when the capture element is actually foreshortened. As illustrated, each individual element 66 has a pair of weakened regions which result in a generally U-shaped expanded structure. As described hereinafter with respect to the method, such an expanded cage structure will both place radially expansive forces against the aortic or other lumenal wall in which they are extended. Such expansion force will assist in guidewire exit when the guidewire is being advanced subintimally. Additionally, after the guidewire exits and passes through the expanded guidewire capture element, the capture element may be collapsed to capture the guidewire and allow the guidewire to be drawn out through the contralateral lumen as the capture catheter is withdrawn.

Figure 9:
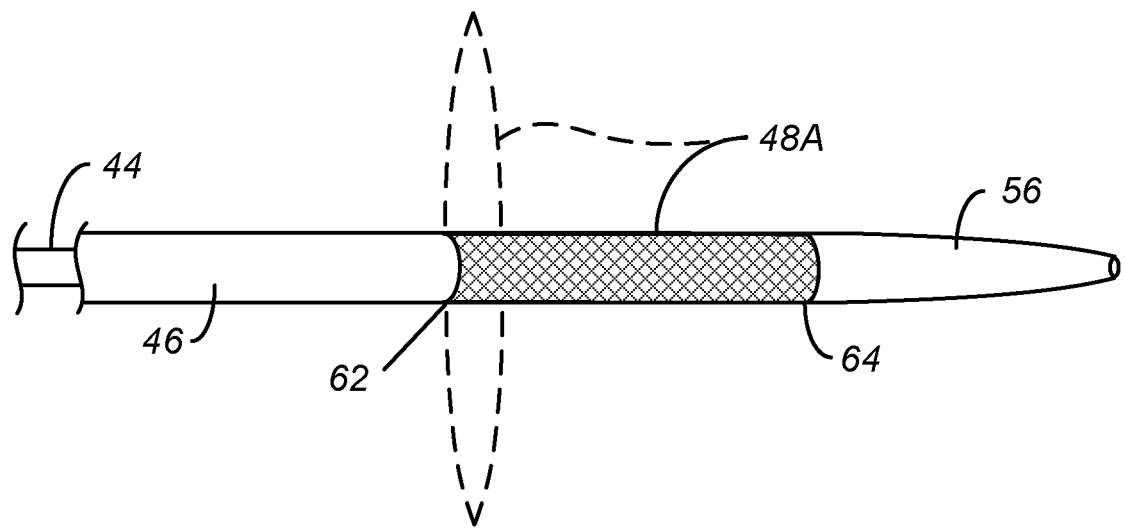
FIGS. 9 and 10 illustrate alternative guidewire capture elements which can be employed on the guidewire capture catheters of the present invention.
Figure 10:
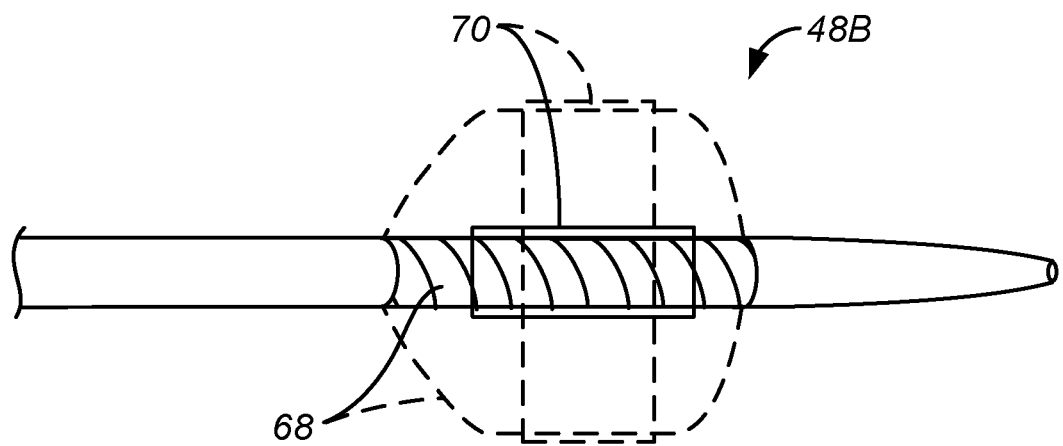

Referring to FIGS. 9 and 10, the expandable guidewire capture element may have a variety of specific implementations. As shown in FIG. 9, instead of discreet axial elements which fold upon foreshortening, an alternative capture element 48A may comprise a polymeric braided structure which will regularly expand into a generally disk geometry (shown in broken line) when the inner tube 44 and outer tube 46 are closed together.

Figure 11:
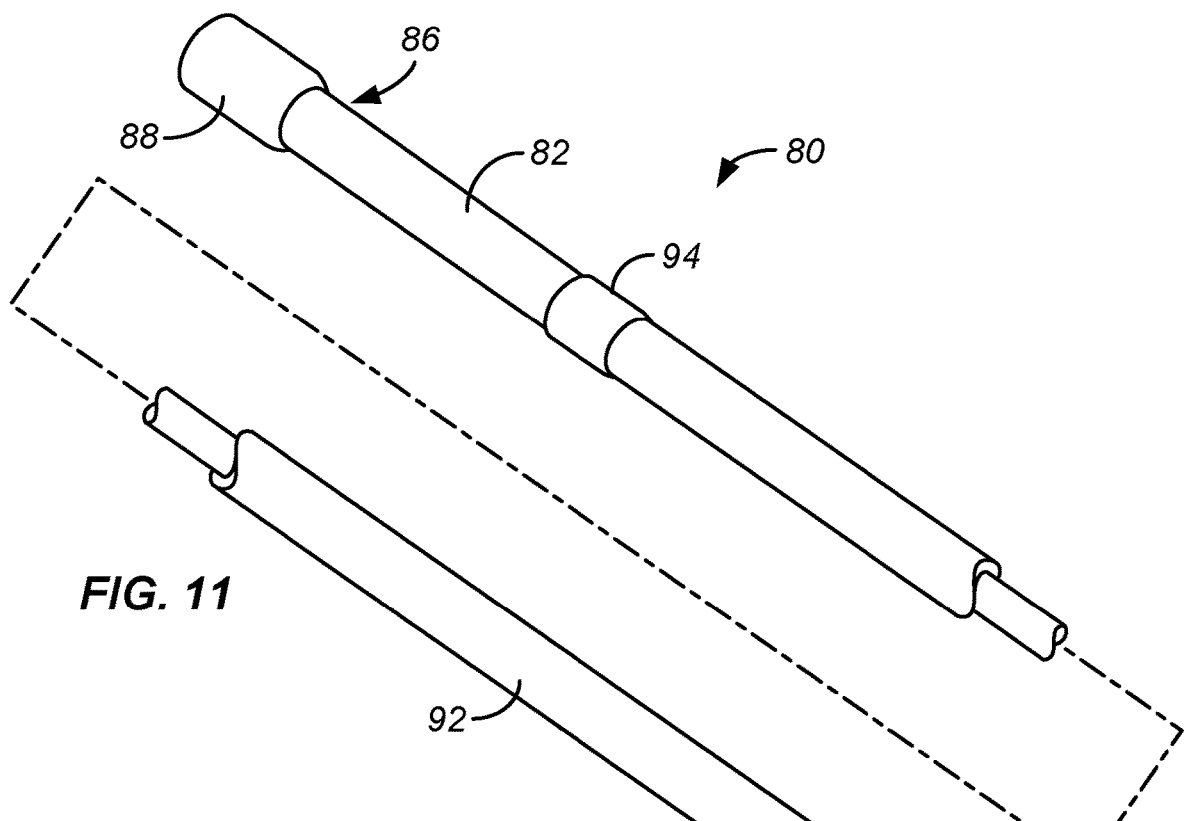
FIG. 11 illustrates an exemplary prosthesis delivery catheter constructed in accordance with the principals of the present invention.

A further exemplary alternative as shown in FIG. 10 where an expandable guidewire capture element 48B comprises a balloon 68 optimally covered by a lattice structure 70 which can expand with the balloon. The balloon and lattice are show in their full expanded configurations in full line and their expanded configurations in broken line. The presence of the lattice 70, which can generally have a stent-like pattern or restructure, can provide a more positive transmission of force to the aortic or other wall in which the capture element is being expanded. Additionally, the lattice can help capture a guidewire which is advanced to the capture element Referring now to FIGS. 11-13, a first exemplary delivery catheter constructed in accordance with the principles of the present invention will be described. The delivery catheters are intended to deliver the tubular prosthesis described previously into and over a Carina in order to stent or graft regions of the branching vessels on either side of the Carina. The first delivery catheter embodiment 80 comprises a catheter body 82 having a distal end 84 and a proximal end 86. A handle or hub 88 is disposed at the proximal end 86 of the catheter body and a guidewire port 90 is provided at the distal end 84. Catheter 80 will be configured for advancement over the crossing guidewire which has been placed from the ipsilateral lumen to the contralateral lumen over the Carina as will be described below.

Figure 12:
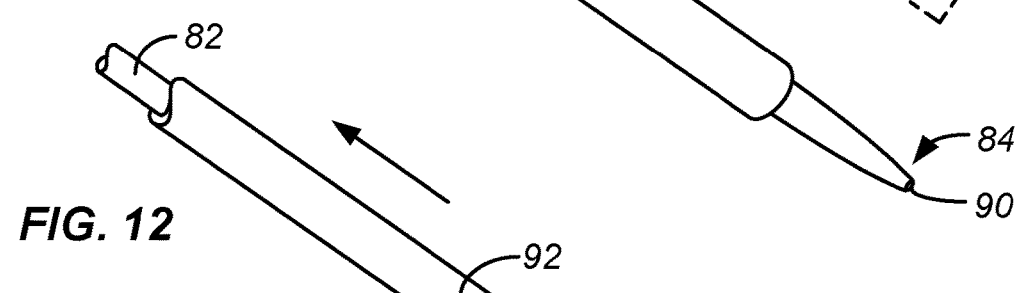
FIGS. 12 and 13 illustrate the retraction of a single sheath to release the tubular prosthesis from the catheter of FIG. 11.
Figure 13:
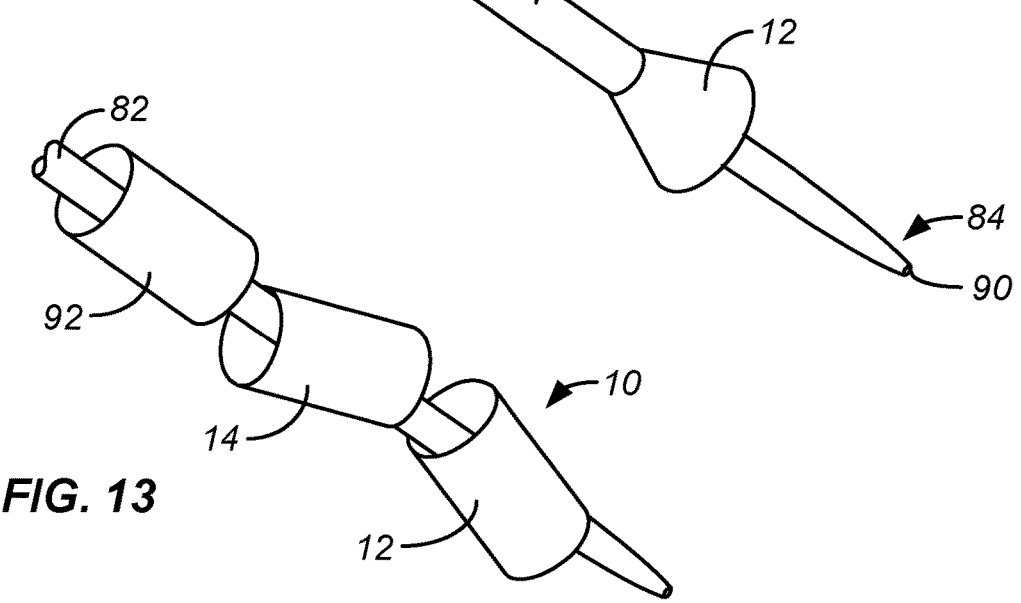

The retractable sheath 92 is coaxially mounted over the catheter body 82 and has a sheath handle 94 which allows the retraction of the sheath relative to the catheter body. The tubular prosthesis 12 (FIGS. 12 and 13) is initially maintained beneath a distal end or portion of the retractable sheath 92 where it remains as the catheter is being advanced over the guidewire to the region over the Carina. The sheath 92 may be then be proximally retracted, as shown in FIG. 12, so that the first segment 12 of the tubular prosthesis is released and begins to self-expand at the desired location. Continued retraction of the sheath 92, as show in FIG. 13, results in full release of the prosthesis 10, including both the first segment 12 and the second segment 14, as shown in FIG. 13. Complete deployment of the tubular prosthesis will, of course, occur when the catheter body 82 is retracted from within the interior of the prosthesis. Additionally, of course, the guidewire will also be fully retracted but the guidewire will generally not inhibit the prosthesis from fully bending and folding within the target anatomy.

Figure 14:
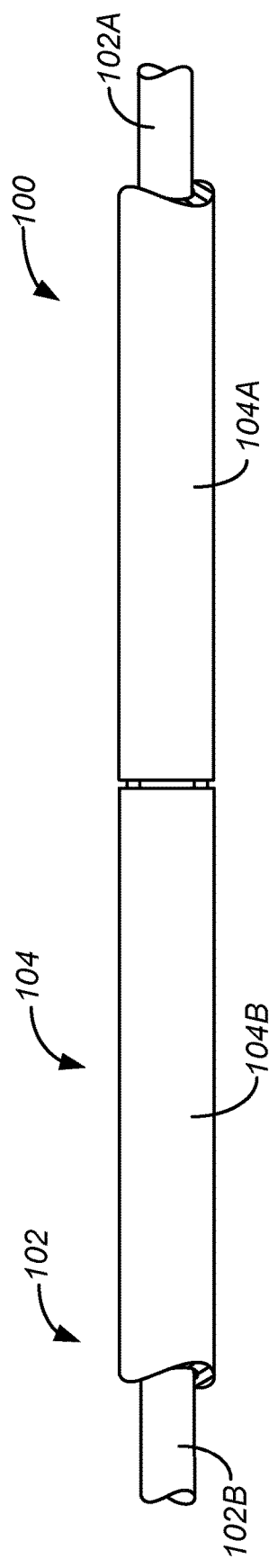
FIG. 14 illustrates an alternative sheath structure for the prosthesis delivery catheter of the present invention.
Figure 15:
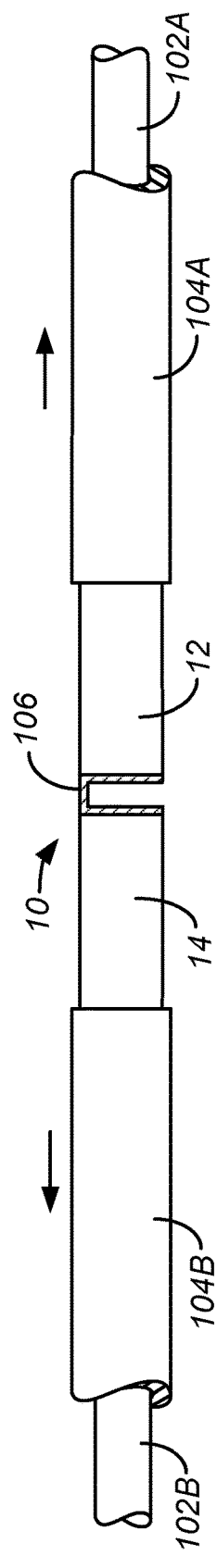
FIGS. 15 and 16 illustrate the retraction in opposite directions of two portions of the sheath to release a prosthesis therefrom.
Figure 16:
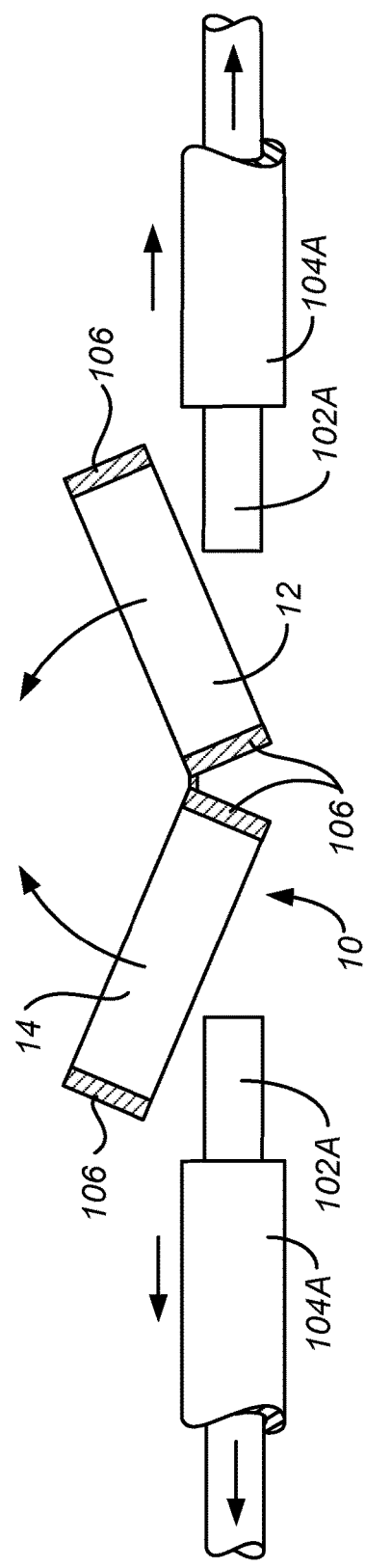

Referring now to FIGS. 14-16, a second exemplary embodiment of the delivery catheter 100 constructed in accordance with the principles of the present invention will be described. The delivery catheter 100 includes a catheter body 102 which is preferably divided into an ipsilateral portion 102A and a contralateral portion 102B. The delivery catheter will further comprise a sheath 104 which is also divided into an ipsilateral portion 104A and a contralateral portion 104B. The tubular prosthesis 10 was initially constrained by the sheath assembly with a full width ipsilateral portion 104A covering the first segment probe of the stent and the contralateral portion 104B covering the second segment 14 of the prosthesis. Other than that shown in FIGS. 14-16, it will be appreciated that the sheath portions 104A and 104B will meet at a point which is generally in the middle of the catheter 100 and catheter body 102 so that the catheter may be deployed completely from the entry sheath in the ipsilateral lumen to the exit sheath and the contralateral lumen. Each sheath will be accessible external to the patient so that the sheaths may be retracted to deploy the tubular prosthesis 10, generally as shown in FIG. 15 and FIG. 16.

The tubular prosthesis 10 will usually include radiopaque markers 106 near its middle and in each end to facilitate positioning of the stent at the desired location over the carina C of the bifurcated lumens. Alternatively or additionally, the depict markers could be provided on the sheath and/or the catheter body.

Retracting the ipsilateral sheath portion 104A toward the ipsilateral vasculature and retracting the contralateral sheath portion 104B toward the contralateral vasculature will result in a symmetric release of the tubular prostheses as shown in FIGS. 15 and 16.

While it would be possible to deliver the sheath in this way using a continuous catheter body 102 which would remain within the tubular prosthesis 10, such deployment would require that the catheter body be separately withdrawn from within the tubular prosthesis in order to allow the prosthesis to fully deploy. Thus, in many embodiments, it will be preferred to provide the catheter body 102 as a separate ipsilateral portion 102A and contralateral portion 102B. In this way, the separate portions of the catheter body 102 may also be separately retracted in ipsilateral and contralateral directions from within the tubular prosthesis in order to permit full deployment of the tubular prosthesis, as shown in FIG. 16B. In such embodiments, ipsilateral components of the delivery catheter 100 will eventually be withdrawn through the ipsilateral access sheath or contralateral portions of the delivery catheter will be withdrawn through the contralateral access sheath.

Figure 17:
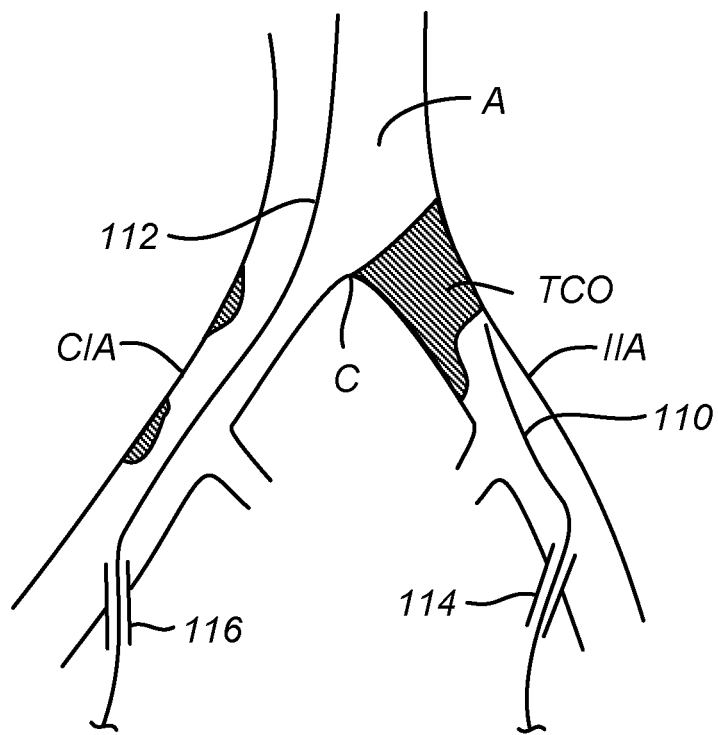
FIGS. 17-26 illustrate delivery of a tubular prosthesis over a carina in an aortic bifurcation in accordance with the principals of the methods of the present invention.

Referring now to FIGS. 17-26, delivery of the tubular prosthesis 10 of the present invention in accordance with an exemplary method of the present invention will be described. Initially, as shown in FIG. 17, a crossing guidewire 110 is placed into the ipsilateral iliac artery IIA through an access sheath 114. The crossing guidewire is advanced until it reaches a downstream side of a chronic total occlusion. A second, contralateral guidewire 112 is advanced into the contralateral iliac artery CIA through an access sheath 116 and advanced typically until it reaches the aorta A.

Figure 18:
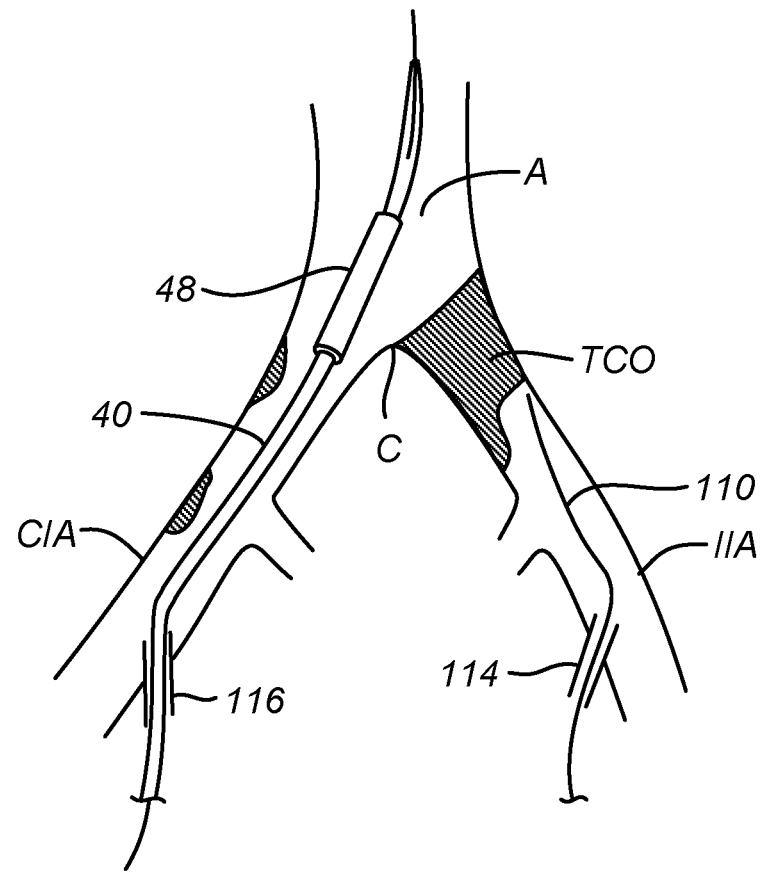

As shown in FIG. 18, the guidewire capture catheter 40 is then advanced through the access sheath 116 over the contralateral guidewire 112 to position the expandable guidewire capture element 48 in the aorta in a region above the Carina and near the upstream side of the Chronic total Occlusion.

Figure 19:
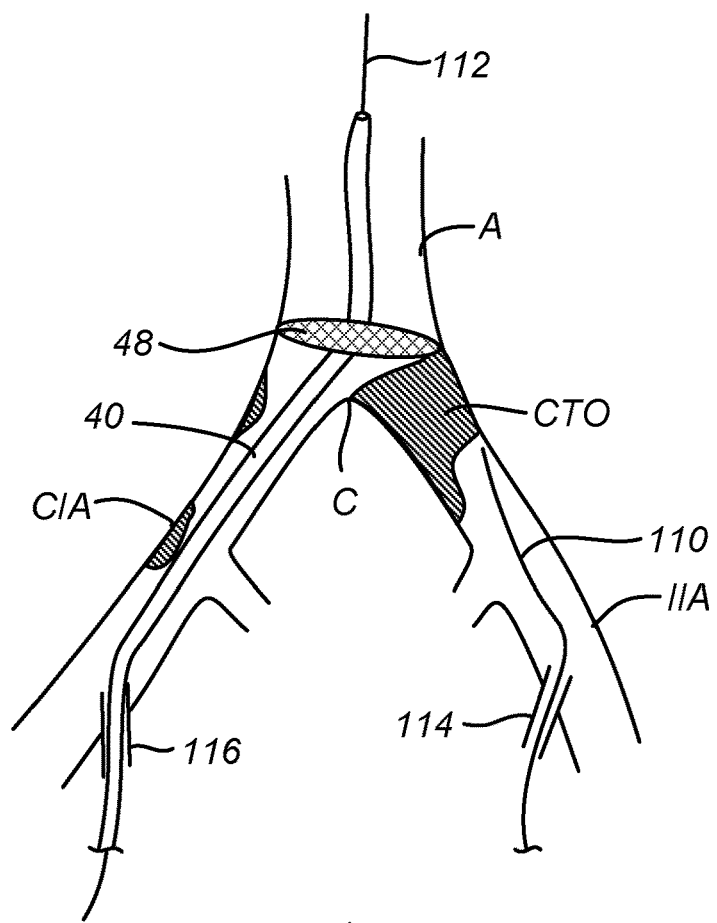

As shown on FIG. 19, the expandable guidewire capture element has been radially expanded so that it engages the aortic wall circumferentially along the line generally aligned with the upstream side of the chronic total occlusion. The expanded guidewire capture element implies an expansive force against the aortic wall, and in particular provides tension and a backstop along the upstream side of the chronic total occlusion CTO.

Figure 20:
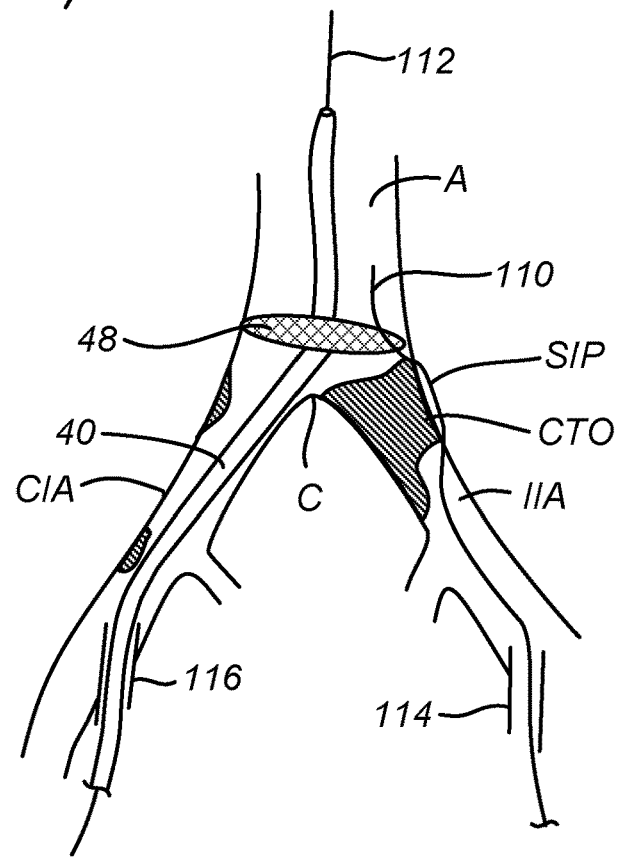

After deployment of the expandable guidewire capture element 40, the crossing guidewire 110 may be advanced past the chronic total occlusion CTO as shown in FIG. 20. Typically, the crossing guidewire 110 will follow a sub intimal path SIP, where the engagement of the capture element 48 facilitates reentry of the crossing guidewire 110 into the aortic lumen, as illustrated. Not only does the expanded guidewire capture element 48 facilitate reentry of the crossing guidewire, the element can also capture a distal end of the guidewire, as will be described with reference to FIG. 21.

Figure 21:
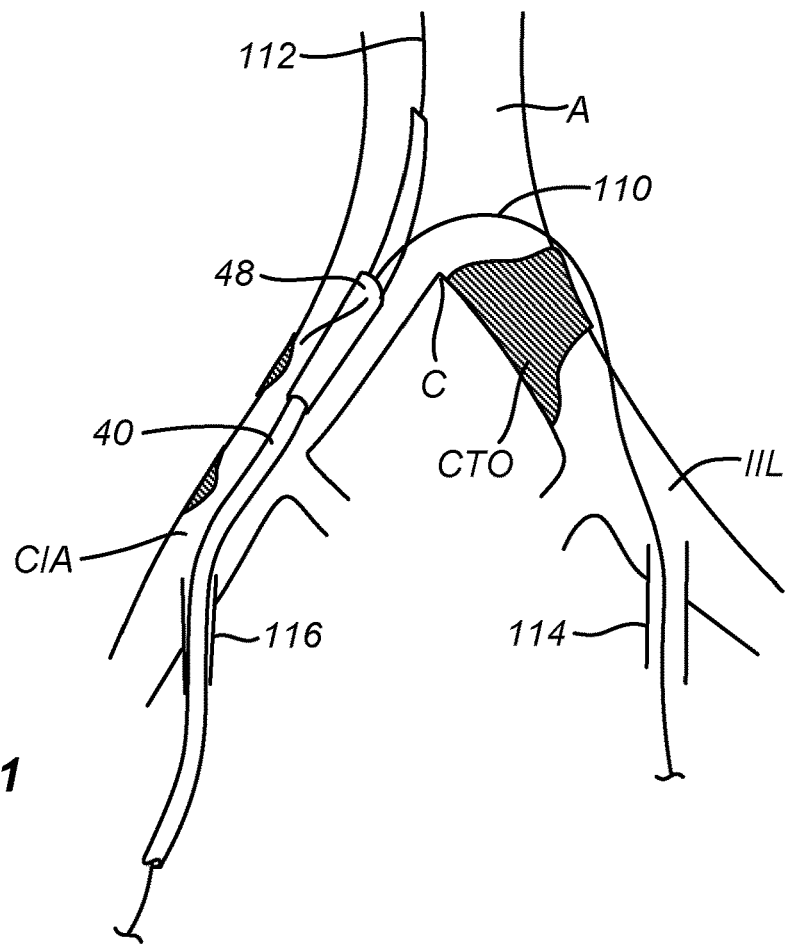
Figure 22:
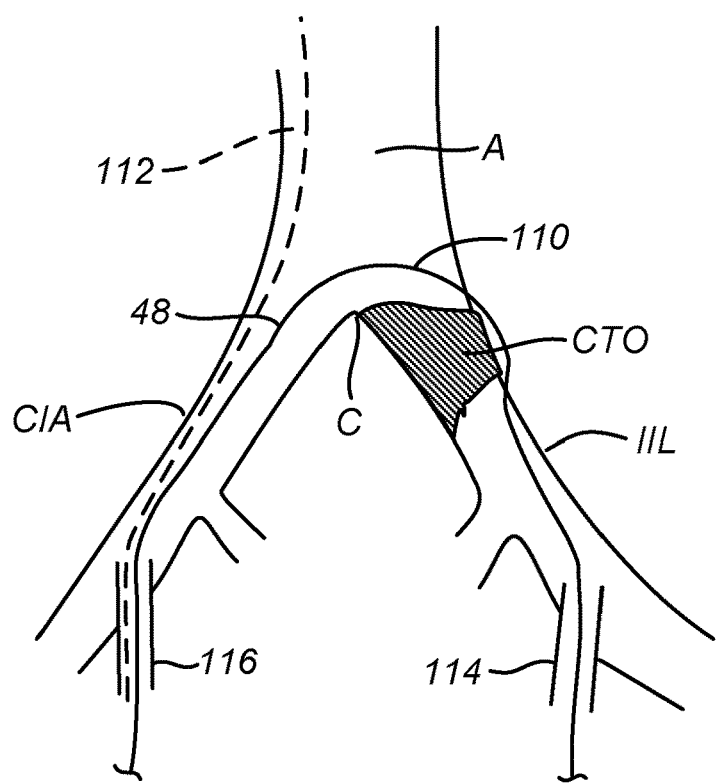

As shown in FIG. 21, the expandable guidewire capture element 48 may be collapsed over the guidewire to firmly engage the guidewire so that the catheter may be used to pull the guidewire over the carina C. By completely withdrawing the guidewire capture catheter 40 from the contralateral iliac aorta and through the access sheath 116, as shown in FIG.

22, the crossing guidewire 110 will be deployed to cross the carina C with one end accessible through the ipsilateral access sheath 114 and the other end accessible through the contralateral access sheath 116. Optionally, the contralateral guidewire 112 may be left in place to establish further access if needed. For convenience, the contralateral guidewire 112 will not be shown in the remainder of the figures.

Figure 23:
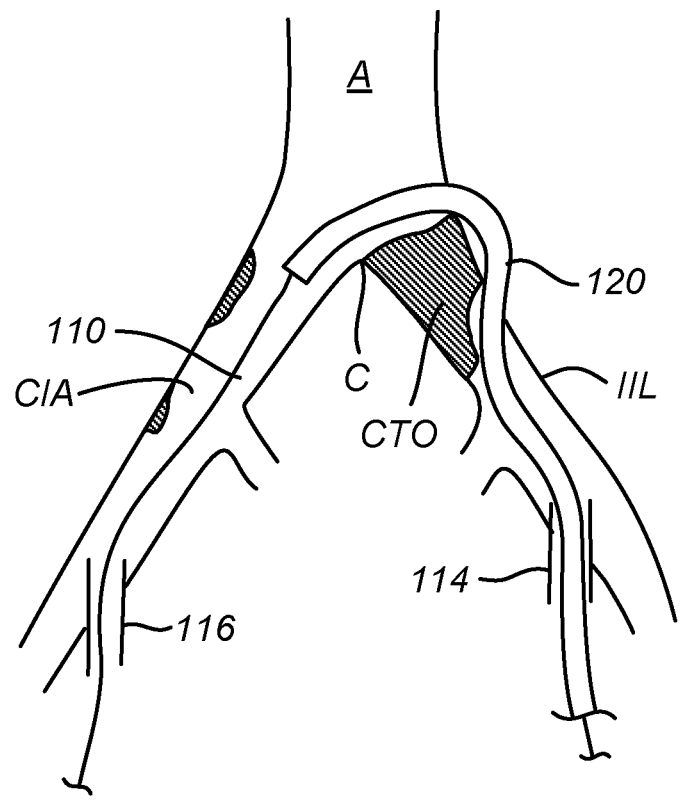

As show in FIG. 23, optionally a pre-shaped guide catheter 120 may be advanced through the ipsilateral access sheath over the guidewire to define a path through or past the chronic total occlusion CTO.

Figure 24:
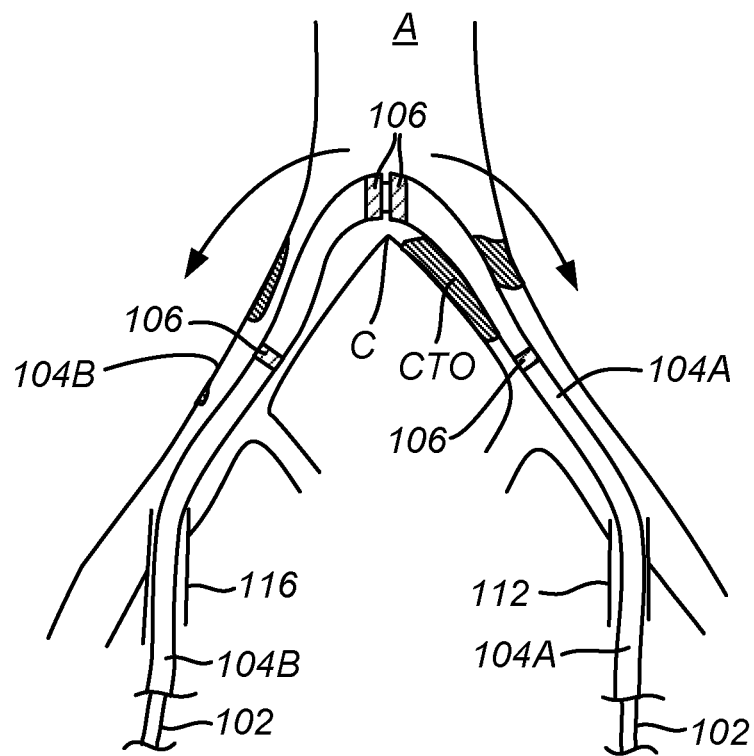
Figure 25:
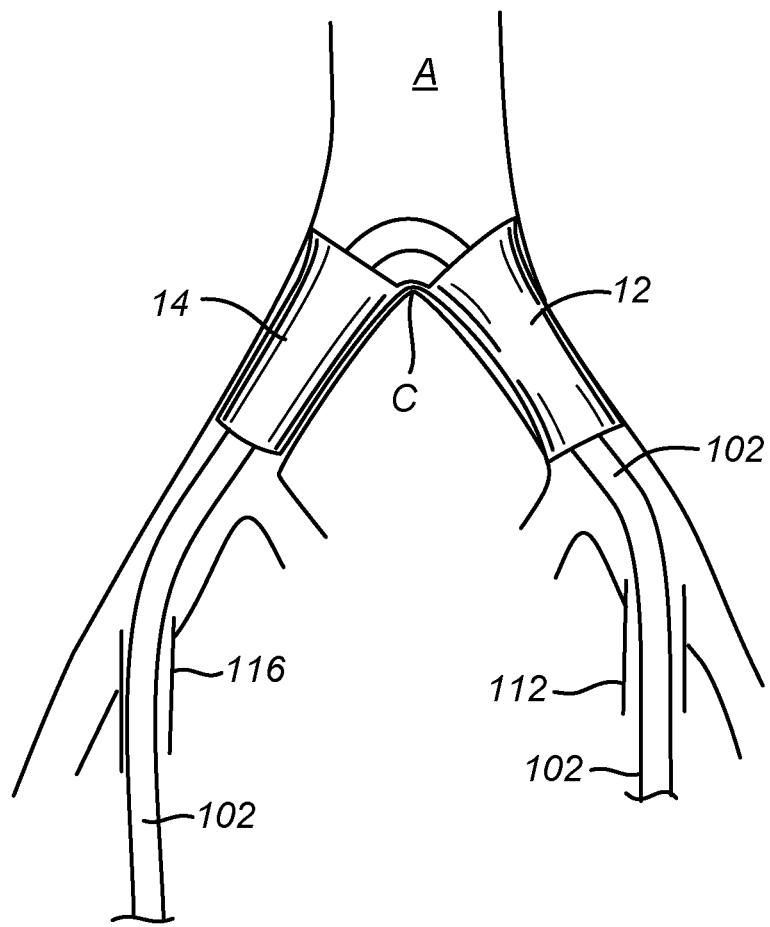
Figure 26:
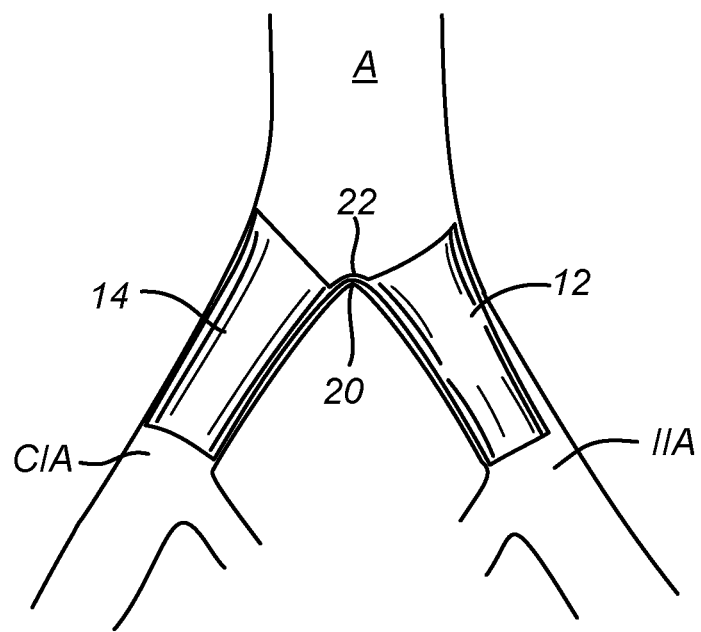

Either with or without the guide catheter, a prosthesis delivery catheter may then be introduced using the previously placed crossing guidewire 110. As shown in FIG. 24, the delivery catheter 100 which has a pair of sheath portions 104A and 104B is used for this example. After positioning the delivery catheter 100 over the carina C, the ipsilateral sheath portion will be accessible through the ipsilateral access sheath 112 and the contralateral sheath portion 104B will be available through the contralateral access port 116. The access sheaths may then be withdrawn in ipsilateral and contralateral directions, respectively, allowing the tubular prosthesis segments 12 and 14 to radially expand in situ, as shown in FIG. 25. As shown in FIG. 25, the catheter body 102 of the delivery catheter is a single element and will remain in place after the tubular prosthesis has radially expanded.

The catheter body 102 may be withdrawn through either of the access sheaths 112 or 116, the crossing guidewire in place. The crossing guidewire can also be withdrawn, leaving the fully deployed prosthesis 110 in place with the first segment 112 in the Ipsilateral Iliac Artery in the second segment 14 present in the Contralateral Iliac Artery. The stent deploys with the hinge region 22 over the carina C.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A delivery catheter system comprising:
   a self-expanding tubular prosthesis having a side opening and configured to be delivered in a linearized arrangement and draped over a delivery body to assume a non-linear configuration over a patient's carina to position the opening at an aorta where the aorta branches into the ipsilateral and contralateral iliac arteries; and
   a catheter body having a distal end and a proximal end, wherein the self-expanding tubular prosthesis is mounted over the catheter body so that the prosthesis may be positioned over the carina with a distal portion of the catheter body in the contralateral artery and a proximal portion of the catheter body in the ipsilateral artery; and
   a sheath configured to be disposed coaxially over the catheter body to radially constrain the self-expanding tubular prosthesis in the linearized arrangement so that retraction of the sheath allows the tubular prosthesis to expand with the opening centered at the aorta.

2. A delivery catheter system as in claim 1, wherein the tubular prosthesis comprises a self-expanding metal scaffold.

3. A delivery catheter system as in claim 2, wherein the self-expanding metal scaffold is covered by a graft material.

4. A delivery catheter system as in claim 1, wherein the self-expanding tubular prosthesis has a hinge region in a middle region thereof aligned with the opening.

5. A delivery catheter system as in claim 4, wherein the hinge region comprises a tether.

6. A delivery catheter system as in claim 1, wherein the tubular prosthesis comprises separate, unjoined segments.

7. A delivery catheter system as in claim 1, wherein the sheath includes a distal portion which at least partially covers a distal segment of the tubular prosthesis and a proximal segment which at least partially covers a proximal segment of the tubular prosthesis, wherein the distal portion may be retracted distally to release the distal segment and the proximal portion may be retracted proximally to release the proximal segment.

8. A delivery catheter system as in claim 1, wherein the sheath comprises a single, continuous structure which at least partially covers both distal and proximal segments of the tubular prosthesis so that the entire sheath may be retracted in a single direction to release both segments of the tubular prosthesis.

* * * * *